United States Patent
Merkel

(10) Patent No.: US 10,434,287 B2
(45) Date of Patent: Oct. 8, 2019

(54) TRANSRADIAL CELIAC ARTERY CATHERER

(71) Applicant: Cook Medical Technologies LLC, Bloomington, IN (US)

(72) Inventor: Clint Merkel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 504 days.

(21) Appl. No.: 15/096,977

(22) Filed: Apr. 12, 2016

(65) Prior Publication Data

US 2016/0317788 A1    Nov. 3, 2016

Related U.S. Application Data

(60) Provisional application No. 62/153,843, filed on Apr. 28, 2015.

(51) Int. Cl.
*A61M 25/09* (2006.01)
*A61M 25/00* (2006.01)
*A61M 25/01* (2006.01)
*A61M 5/00* (2006.01)

(52) U.S. Cl.
CPC ........ *A61M 25/09* (2013.01); *A61M 25/0041* (2013.01); *A61M 25/0068* (2013.01); *A61M 25/0133* (2013.01); *A61M 25/0152* (2013.01); *A61M 5/007* (2013.01); *A61M 2025/0161* (2013.01); *A61M 2210/127* (2013.01)

(58) Field of Classification Search
CPC .... A61M 2025/0161; A61M 2210/127; A61M 25/0041; A61M 25/0068; A61M 25/0133; A61M 25/0152; A61M 25/09; A61M 5/007
See application file for complete search history.

(56) References Cited

U.S. PATENT DOCUMENTS

| | | | |
|---|---|---|---|
| 5,231,994 | A | 8/1993 | Harmjanz |
| 5,445,625 | A | 8/1995 | Voda |

(Continued)

FOREIGN PATENT DOCUMENTS

WO    WO 2004/032791 A1    4/2004

OTHER PUBLICATIONS

Adler, David H. MD et al., "Transradial Cardiac Catheterization", Medscape Reference, Updated Jan. 24, 2014.

(Continued)

*Primary Examiner* — Brandy S Lee
(74) *Attorney, Agent, or Firm* — Woodard, Emhardt, Henry, Reeves & Wagner, LLP

(57) ABSTRACT

The present disclosure provides unique products and methods for accessing the vasculature of a patient. The catheter arrangements disclosed herein include a distal segment having a first substantially straight portion, a laterally extending portion, a tip-opposing portion, a tip-deflecting portion and a distal tip. The first substantially straight portion has a longitudinal axis that extends between the tip-opposing portion and the distal tip. The tip-deflecting portion extends transverse to and passes or crosses through the longitudinal axis and deflectably supports the distal tip such that the distal tip can deflect towards the tip-opposing portion upon an external force.

19 Claims, 11 Drawing Sheets

(56) References Cited

U.S. PATENT DOCUMENTS

| | | | |
|---|---|---|---|
| 5,876,385 A * | 3/1999 | Ikari | A61M 25/0041 |
| | | | 604/523 |
| 6,355,026 B1 | 3/2002 | Mick | |
| 6,620,150 B2 | 9/2003 | Kiemeneij | |
| 7,729,782 B2 | 6/2010 | Williams et al. | |
| 2006/0036218 A1* | 2/2006 | Goodson, IV | A61M 25/0054 |
| | | | 604/264 |
| 2009/0288368 A1 | 11/2009 | Waller et al. | |
| 2014/0025041 A1 | 1/2014 | Fukuoka et al. | |
| 2014/0088566 A1 | 3/2014 | Dangoisse | |
| 2014/0276605 A1 | 9/2014 | Furqan et al. | |

OTHER PUBLICATIONS http://www.terumois.com/products/catheters/optitorque.html.; Optitorque Coronary Diagnostic Catheters Pamphlet, Printed Jun. 2009 for Terumo Interventional Systems.

Rao, Sunil V., MD et al., "The Transradial Approach to Percutaneous Cornoary Intervention", Journal of the American College of Cardiology, vol. 55, No. 20, 2010.

Springer Science & Business Media, New York, Harrigan, M.R. and Deveikis, J. P, "Handbook of Cerebrovascular Disease and Neurointerventional Technique", pp. 99-131 (2013).

\* cited by examiner

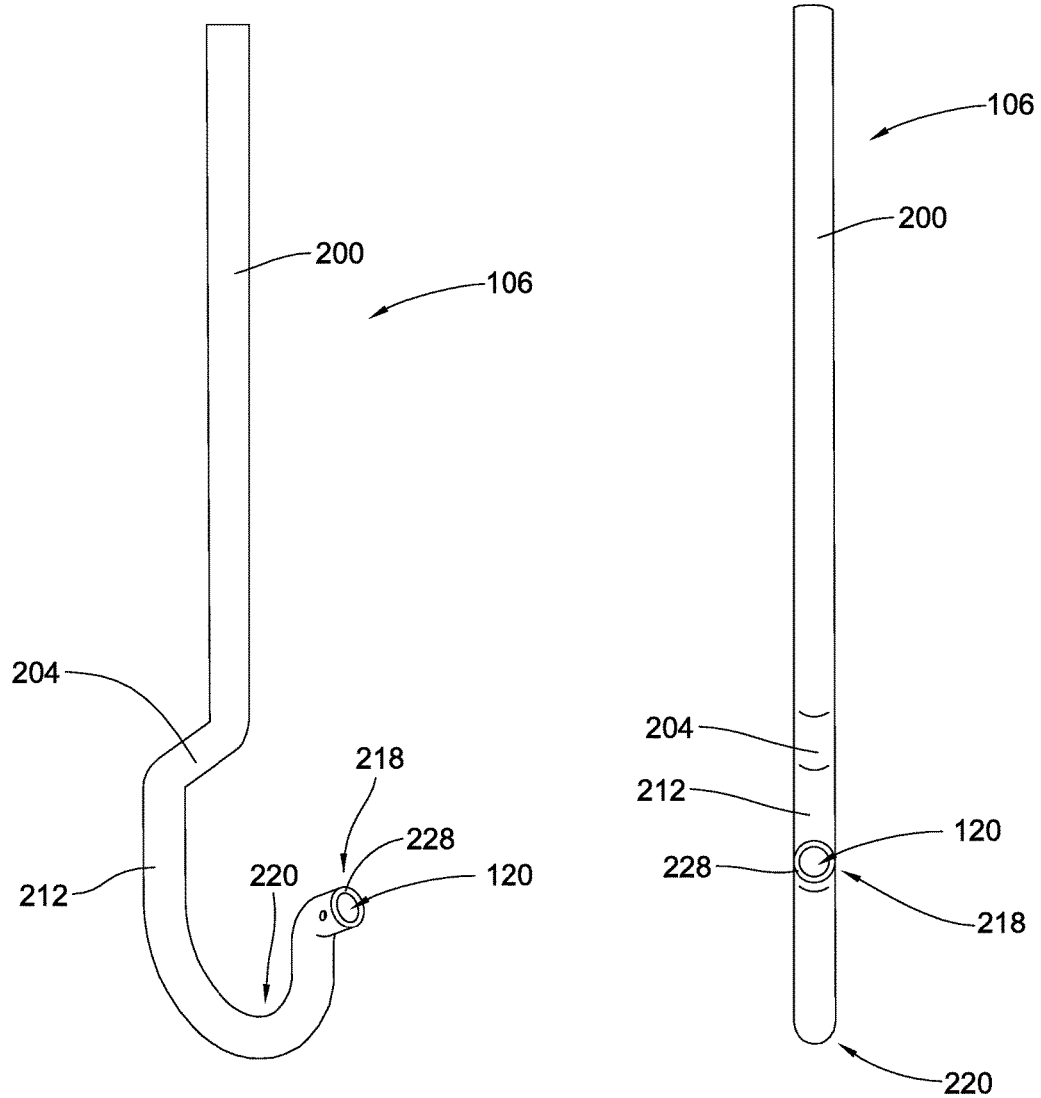

TRANSRADIAL CELIAC ARTERY CATHERER

BACKGROUND

The present disclosure pertains generally to medical devices. Catheters are a type of medical device that include a variety of elongated and generally hollow bodies that can be introduced into a patient for many different purposes. For example, catheters may be used to supply therapeutic fluids, to perform diagnostic or surgical procedures, for implantation of therapeutic devices, and for the introduction of instruments.

Preshaped catheters are known to be used for procedures, such as percutaneous intervention, in which the catheter can serve as a guide for other catheters or devices, such as a balloon catheter. Preshaped catheters generally include a distal end which has been shaped or configured to carry out a specific procedure for which the device is designed. Current catheter designs, however, are not suitable for accessing certain locations within the body of a patient from some approaches. Therefore, new catheter configurations and associated methods are desired.

SUMMARY

A femoral approach catheterization is used in many instances to access the vasculature of a patient when the target site is in the abdomen. For instance, a femoral approach is often used when delivering implantable devices into the abdominal aorta, such as a stent graft for the treatment of an abdominal aortic aneurysm. When performing a femoral approach, a medical professional will many times access the femoral artery and advance a guidewire superiorly through the femoral artery and into the abdominal aorta. Advantageously, this approach is a substantially direct path that is free of tortuous vasculature, in many patients, and does not require instruments of significant length which can become cumbersome to handle in the operating suite. However, because of the size and location of the femoral artery, applying pressure to the access site in the femoral artery can be difficult and access-site bleeding complications post-procedure are possible and do occur. Additionally, patients who have undergone a transfemoral catheterization often must maintain a supine position for an extended period of time after the procedure in order to achieve hemostasis.

To address these problems, Applicant has investigated a transradial approach for percutaneous intervention, in particular for accessing the branch vessels of the abdominal aorta. A transradial approach includes inserting and advancing a catheter through an artery in the arm, such as the brachial artery, and into the aorta at the aortic arch. The catheter can then be advanced through the thoracic aorta and into the abdominal aorta. Advantageously, a transradial approach can lead to fewer instances of access-site bleeding complications due to the decreased size and the superficial (i.e., closer to the skin) location of the radial artery. These factors make it easier to apply compression to the radial artery to achieve hemostasis.

Because current catheters are either inadequate for a transradial approach for accessing the vasculature of the abdomen or are difficult to orient to achieve access to the vasculature of the abdomen from a transradial approach, the present disclosure provides new catheter designs and methods for accessing the abdominal vasculature for a transradial approach.

The present disclosure pertains generally to medical devices and methods useful for accessing vascular branches in the body of a patient. In particular, the present disclosure provides devices and methods for accessing the branch vessels of the abdominal aorta. The figures and associated text of the present disclosure provide methods of accessing a branch vessel of the abdominal aorta of a patient, comprising advancing a catheter body in an insertable configuration into an artery of an arm of the patient and through the body of the patient towards and into the abdominal aorta, the catheter body configurable from the insertable configuration to a preformed configuration; configuring a distal segment of the catheter body into the preformed configuration, wherein the distal segment in the preformed configuration has a length that includes a first substantially straight portion, a laterally extending portion, a tip-opposing portion, a tip-deflecting portion, and a distal tip, wherein the first substantially straight portion has a longitudinal axis, wherein the laterally extending portion is positioned distally of the first substantially straight portion along the length of the distal segment and extends laterally away from the longitudinal axis, wherein the tip-opposing portion is positioned distally of the laterally extending portion along the length of the distal segment and extends substantially parallel to and offset from the longitudinal axis, wherein the tip-deflecting portion is positioned distally of the tip-opposing portion along the length of distal segment and extends laterally past the longitudinal axis, wherein the distal tip is positioned distally of the tip-deflecting portion along the length of the distal segment and is diametrically opposed to the tip-opposing portion relative to the longitudinal axis, wherein the tip-deflecting portion deflectably supports the distal tip relative to the tip-opposing portion so that the distal tip is deflectable towards the tip-opposing portion upon an external force; and positioning the distal tip within the branch vessel of the abdominal aorta. In the present disclosure, advancing the catheter body in an insertable configuration can include advancing the catheter body in an insertable configuration over a guidewire. Additionally, configuring a distal segment of the catheter body into the preformed configuration can include withdrawing the guidewire from within the catheter body so as to configure the distal segment of the catheter body into the preformed configuration. Positioning the distal tip within a branch vessel can include rotating the proximal segment of the catheter body so as to rotate the tip-opposing portion and distal tip around the longitudinal axis. Positioning the distal tip within a branch vessel can also or alternatively include translating (e.g., sliding by pushing or pulling) the proximal segment so as to translate the distal segment and distal tip.

The present disclosure also provides catheter designs comprising a catheter body having a proximal segment and a distal segment; the distal segment having a preformed configuration and a length that includes a first substantially straight portion, a laterally extending portion, a tip-opposing portion, a tip-deflecting portion and a distal tip; the first substantially straight portion having a longitudinal axis; the laterally extending portion positioned distally of the first substantially straight portion along the length of the distal segment and extending laterally away from the longitudinal axis; the tip-opposing portion positioned distally of the laterally extending portion along the length of the distal segment and extending substantially parallel to and offset from the longitudinal axis; the tip-deflecting portion positioned distally of the tip-opposing portion along the length of distal segment and extending laterally across the longitudinal axis when projected onto a plane with the longitudinal axis and the laterally extending portion; the distal tip positioned distally of the tip-deflecting portion along the length of the distal segment and laterally opposite the tip-opposing portion relative to the longitudinal axis; wherein the distal tip is deflectably supported by the tip-deflecting portion and is deflectable towards the tip-opposing portion.

Additionally, the present disclosure provides catheter arrangements comprising a catheter body having proximal segment and a distal segment, the proximal segment substantially straight under a free state and a distal segment having a curved shape under a free state, the distal segment including a first substantially straight portion, a first curved portion, a laterally extending portion, a second curved portion, a tip-opposing portion, a tip-deflecting portion, and a distal tip positioned in that order in a proximal to distal direction along a length of the distal segment; the first substantially straight portion having a longitudinal axis; the first curved portion connecting the first substantially straight portion and the laterally extending portion; the laterally extending portion extending transverse to and laterally away from the longitudinal axis; the second curved portion connecting the laterally extending portion and the tip-opposing portion; the tip-opposing portion extending substantially parallel to and offset from the longitudinal axis; and the tip-deflecting portion connecting the tip-opposing portion and the distal tip; wherein the distal tip is deflectably supported by the tip-deflecting portion so that the distal tip may deflect towards the tip-opposing portion when subjected to an external force.

In the catheters of the present disclosure, the tip-opposing portion can be arranged to rest against an inner surface of the abdominal aorta of a patient and the tip-deflecting portion can be arranged to extend radially across the abdominal aorta and position the distal tip in an opening of a branch vessel extending from the abdominal aorta.

The catheter bodies of the present disclosure can also have the distal tip of the catheter body diametrically opposed to the tip-opposing portion relative to the longitudinal axis. Additionally or alternatively, the longitudinal axis can extend through the tip-deflecting portion, and, in some instances, the longitudinal axis bisects the tip-deflecting portion.

The distal segment of the catheter body can curve through an angle of at least 160° and in some instances no greater than 300°. For example, the first substantially straight portion, laterally extending portion, tip-opposing portion, and tip-deflecting portion can define a curve that extends through 270°. In some instances, the tip-deflecting portion defines a curve that extends through at least 160° and/or has a center of curvature positioned on the longitudinal axis.

The catheter arrangements of the present disclosure can also have a distance of 10 mm or less between the longitudinal axis of the first substantially straight portion and a longitudinal axis of the tip-opposing portion. Alternatively or additionally, the tip-opposing portion can have a length of at least 10 mm.

The present disclosure also provides catheter arrangements comprising a catheter body having proximal segment and a distal segment, the proximal segment substantially straight under a free state and a distal segment having a curved shape under a free state, the distal segment including a first substantially straight portion, a first curved portion, a laterally extending portion, a second curved portion, a tip-opposing portion, a third curved portion, and a distal tip positioned in that order in a proximal to distal direction along a length of the distal segment; the first substantially straight portion having a longitudinal axis; the first curved portion connecting the first substantially straight portion and the laterally extending portion; the laterally extending portion extending transverse to and laterally away from the longitudinal axis; the second curved portion connecting the laterally extending portion and the tip-opposing portion; the tip-opposing portion extending substantially parallel to and offset from the longitudinal axis; and the third curved portion connecting the tip-opposing portion and the distal tip; wherein the longitudinal axis bisects the third curved portion.

The catheters of the present disclosure can have a variety of shapes and sizes. For instance, the catheters of the present disclosure can have a length of at least 110 cm when measured from the distal tip to the proximal end. In each instance, the catheters can have a length of at least 120 cm. Additionally, catheter arrangements of the present disclosure may have a maximum cross-sectional dimension (e.g., outer diameter) of 5 French or less (approximately 1.7 mm or less; 1 French=⅓ mm). The catheter lumen is preferably suitable for slidably receiving a 2.8 French microcatheter (0.93 mm) and/or a 0.038 inch wire (approximately 1 mm). For example, the inner diameter of the lumen defined by the catheter body can be 0.04 inches (1 mm).

The tip-opposing portion of the catheter arrangements disclosed herein can have a length of at least 10 mm. In some instances, the tip-opposing portion has a length between 10 mm and 30 mm. In some particular arrangements, the tip-opposing portion has a length of 20 mm.

In the disclosed catheter arrangements, the tip-opposing portion and tip-deflecting portion of the distal segment can define a shape having a maximum outer dimension of 30 mm or less when measured perpendicular to the longitudinal axis. Additionally or alternatively, the tip-opposing portion and tip-deflecting portion of the distal segment can define a shape having a maximum outer dimension of at least 10 mm when measured perpendicular to the longitudinal axis. For example, the tip-opposing portion and tip-deflecting portion can define a shape having a maximum outer dimension of 18 mm to 20 mm when measured perpendicular to the longitudinal axis. Distal segments of the catheter arrangements disclosed herein can define a shape having a maximum outer dimension of 35 mm or less when measured along a direction perpendicular to the longitudinal axis of the first substantially straight portion of the distal segment.

The catheter arrangements disclosed herein are capable of transmitting a rotational force (i.e., torque) applied to the proximal segment to the distal segment of the catheter. In many instances, the catheter body comprises a reinforcing member such as an embedded metal strand, coil and/or braid to decrease the degree of torsional deflection. Alternatively or additionally, the catheter body of the present disclosure may comprise layers of material with a metal positioned between those layers. For example, the catheter body may comprise a PTFE (e.g., Teflon) inner layer, a wire coil or braid of stainless steel over the PTFE, and a polyamide (Nylon) outer layer so that the wire coil or braid is sandwiched between the polyamide outer layer and a PTFE inner layer. PVC may also be used, such as for the outer layer.

The reinforcing member may extend to the distal tip of the catheter or may terminate at a location proximal to distal tip. For example, the reinforcing member may be embedded in the wall of the catheter, particularly through the first substantially straight portion, the laterally extending portion, the tip-opposing portion and at least a portion of the tip-deflecting portion. The reinforcing member can be arranged to provide column strength and/or torsional stiffness to the catheter. In many instances, catheter arrangements having a length of 110 cm or more include a reinforcing member. Advantageously, including a reinforcing member in catheters having a length of 110 cm or more can improve an operator's ability to push the catheter through the vasculature and rotate the distal segment of the catheter when it is positioned within the body of the patient.

A variety of materials can be used in forming the catheter body. As discussed above, PVC and PTFE materials may be used in forming one or more layers of the catheter body. Additionally, nylon may be used in forming portions of the catheter body.

The proximal segment of the catheter bodies disclosed herein may have different material properties than those of the distal segment. For example, a catheter body may have a proximal segment that is torsionally stiffer (i.e., more resistant to torsional deflection) than the distal segment. Alternatively or additionally, the distal segment of the catheter body may be more flexible than the proximal segment. For example, the material(s) forming the catheter body may vary by hardness along the length of the catheter. For instance, the proximal segment may have a Shore durometer hardness of approximately 70-90 D with the distal segment having a hardness of approximately 55-75 D.

The catheter bodies disclosed herein may vary in material along their length. For example, the proximal segment may comprise a first material at the proximal segment and a second material at the distal segment. For instance, nylon 12 may be used for the proximal segment and a nylon-pebax may be used for the distal segment. The material and/or material properties may also vary along the length of the distal segment. For example, the laterally extending portion may comprise a resilient material and the tip-deflecting portion may comprise a flexibly resilient material.

The catheter arrangements disclosed herein may include coatings. For example, the catheter bodies may include a lubricious coating, such as a hydrophilic coating, that reduces the surface friction of the catheter body when it is wetted. Advantageously, lubricious coatings can ease insertion and aid in navigation (e.g., improve pushability) of the catheter body through the anatomy.

The catheter arrangements disclosed herein may also include an atraumatic tip. In many instances, the catheter bodies include a rounded and/or tapered distal tip.

The catheter arrangements disclosed herein may also be made using conventional methods. For example, a portion of the catheter body can be positioned within a groove of a mold or plate, the groove having the desired shape for the portion of the catheter body. The catheter body may be heated prior to and/or while positioned within the groove so that residual stress within the catheter body is removed and the catheter takes a free state in the shape of the groove.

The catheter arrangements disclosed herein can be packaged in sterile form medical packaging. The arrangements can be packaged with the distal segment in a preshaped/preformed configuration or in the insertable configuration. Terminal sterilization of the packaged product may be achieved, for example, by irradiation, ethylene oxide gas, or any other suitable technique, and the materials and other properties of the medical packaging can be selected accordingly.

In one exemplary method of use for the disclosed catheters, access to an artery in the arm of a patient, such as the radial or brachial artery, may be obtained using a needle and an accepted aseptic technique, such as the Seldinger technique. Once access to the vessel is achieved, a steerable guidewire may be advanced through the vessel, through the thoracic aorta and towards the abdominal aorta. Once the steerable guidewire is properly positioned within the aorta, various sheaths and/or catheters may be advanced over the steerable guidewire to position those instruments in the aorta. The catheter bodies described herein may be advanced into the aorta over the steerable guidewire and/or over an emplaced straightening or stiffening wire that straightens out the distal segment of the catheter body into a straightened, insertable configuration. Alternatively, the catheter bodies described herein may be positioned within a sheath, such as a splittable sheath, that retains the catheter body in an insertable configuration during advancement through the vasculature. Once the distal segment of the catheter body is at the target site within the aorta, the straightening wire or splittable sheath may be removed from the distal segment and the distal segment of the catheter body returns to a preformed configuration. The proximal segment of the catheter body may then be manipulated by a medical professional, such as by rotating and/or pushing/pulling the proximal segment, to position the distal tip in a branch vessel opening in the wall of the aorta.

To remove the catheter body from the patient, the catheter body may be pulled proximally out of the body of the patient. In some instances, a straightening wire or sheath may be advanced through the distal segment to substantially straighten out the distal segment so as to ease withdrawal through the vasculature.

Further forms, objects, features, aspects, benefits, advantages, and embodiments of the present disclosure will become apparent from a detailed description and drawings provided herewith.

BRIEF DESCRIPTION OF THE DRAWINGS

FIG. 6 illustrates a perspective view of the distal segment illustrated in FIG. 5.

FIG. 7 illustrates a side view of the distal segment illustrated in FIGS. 5 and 6.

DESCRIPTION OF THE SELECTED EMBODIMENTS

Figure 1:
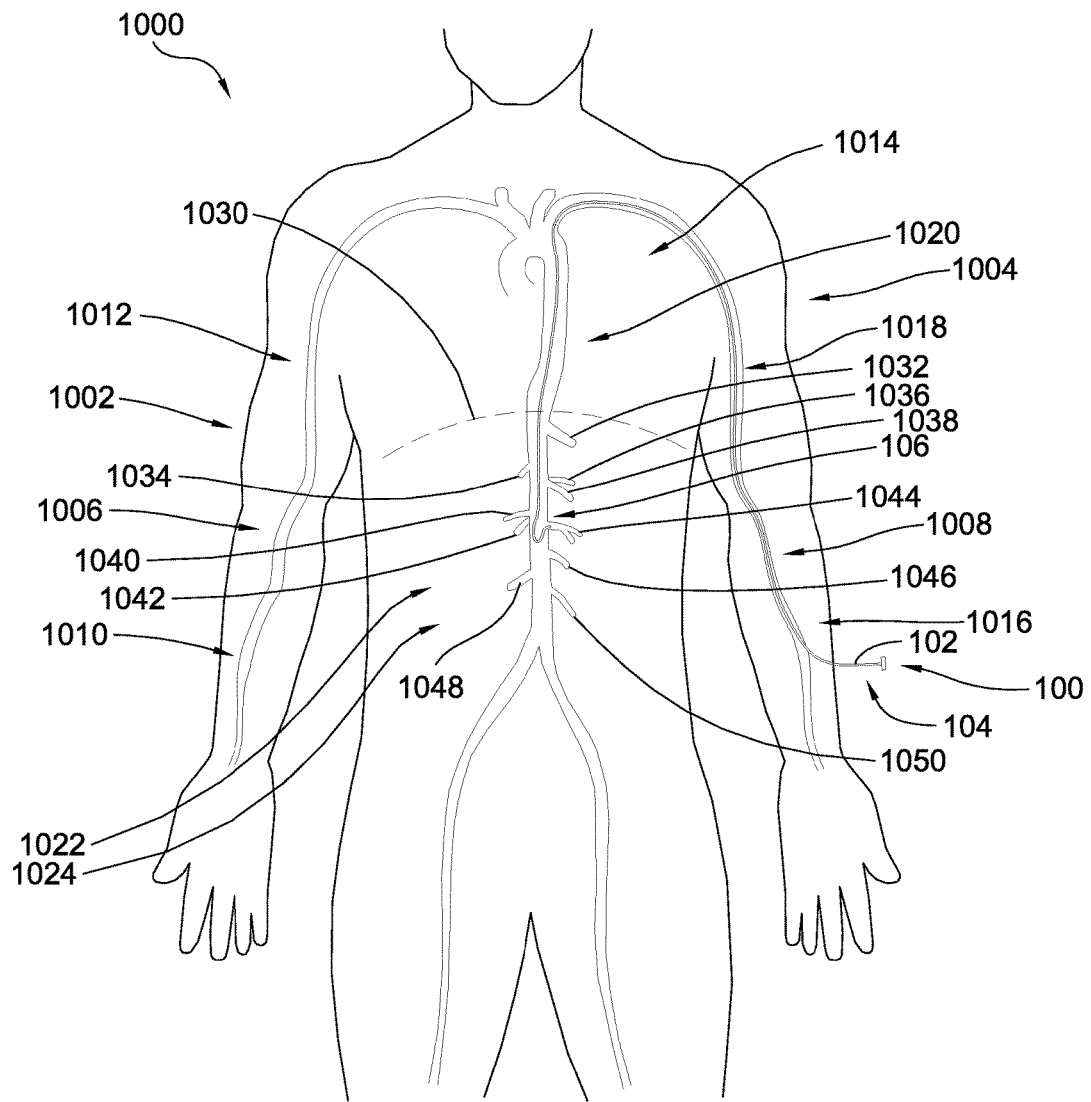
FIG. 1 illustrates a front view of a patient having a catheter of the present disclosure inserted into the vasculature of the patient along a transradial approach.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

FIG. 1 illustrates a front view of a patient 1000. The patient's body includes a right arm 1002 and a left arm 1004 having a right arm artery 1006 and a left arm artery 1008, respectively. The right arm artery 1006 includes a radial artery portion 1010 and a brachial artery portion 1012 extending towards the aortic arch 1014 of the patient. Similarly, the left arm artery 1008 of the patient 1000 includes a radial artery portion 1016 and a brachial artery portion 1018.

Extending inferiorly from the aortic arch 1014 is the descending thoracic aorta 1020 which extends towards the abdominal aorta 1022. After passing through the diaphragm 1030, there are a variety of arterial branches that extend from the abdominal aorta 1022 in the location of the celiac trunk 1024. For instance, the phrenic 1032, common hepatic 1034, gastric 1036 and splenic 1038 arteries extend laterally away from the abdominal aorta 1022. Other branches such as the adrenal 1040, superior mesenteric 1042, renal 1044, gonadal 1046, inferior mesenteric 1048, and lumbar 1050 arteries also extend laterally from the abdominal aorta 1022. These branches supply blood to a variety of organs such as the stomach, spleen, kidneys, liver and intestines.

Figure 2:
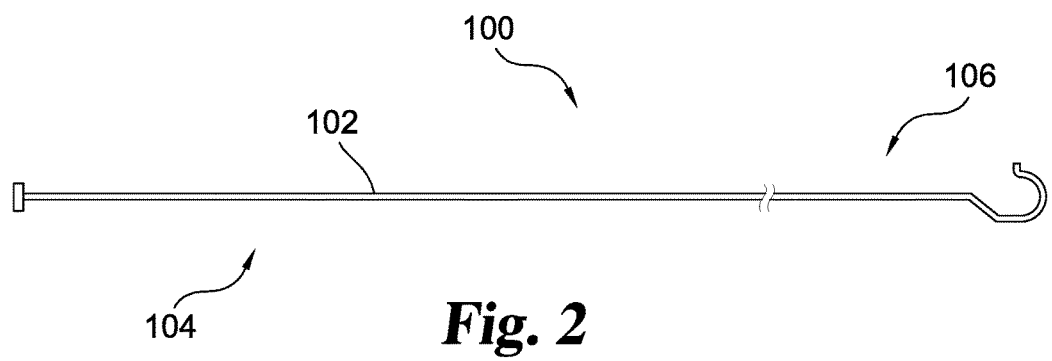
FIG. 2 illustrates a plan view of a catheter of the present disclosure in a preformed configuration that is free of external forces.

Turning now to a description of illustrative embodiments of the present disclosure, FIGS. 1 and 2 illustrate a catheter 100 comprising catheter body 102 having a proximal segment 104 and a distal segment 106. In FIG. 1, the catheter body 102 is illustrated as extending through the radial, brachial and aortic arteries of the patient. FIG. 2 illustrates the catheter 100 under a free state, meaning the catheter 100 and catheter body 102 are substantially free of external forces.

Figure 3:
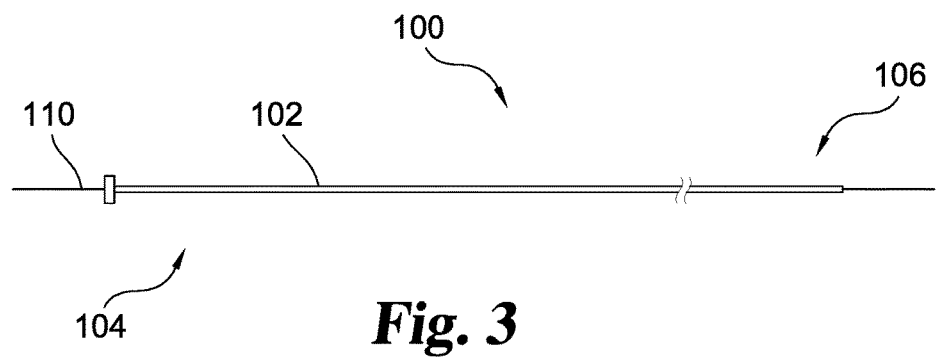
FIG. 3 illustrates a plan view of a catheter of the present disclosure in an insertable configuration with a stiffening wire extending therethrough.
Figure 4:
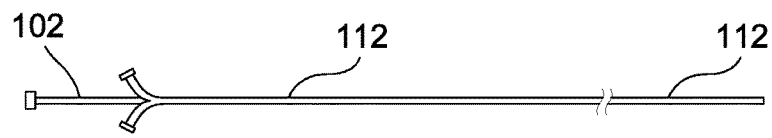
FIG. 4 illustrates a plan view of a catheter of the present disclosure in an insertable configuration with a splittable sheath positioned therearound.

Catheter 100, however, is configurable from the free state, or preformed configuration, illustrated in FIG. 2 to an implanted configuration such as that illustrated in FIG. 1. Additionally, catheter 100 is configurable from a preformed or precurved configurations (e.g., the free state configuration shown in FIG. 2) to a straightened configuration such as that shown in FIG. 3. In the straightened, insertable configuration, the distal segment 106 is substantially straight and free of the curved distal end. The catheter 100 can be configured into the straight configuration shown in FIG. 3 by inserting a guidewire 110 through a lumen of the catheter body 102. Alternatively, the catheter can be configured into a straight configuration by an outer sheath 112, such as a peel away sheath, positioned around the exterior surface of catheter body 102, as illustrated in FIG. 4.

A detailed description of the distal segment 106 of the catheter body will now be made. The portions of the distal segment 106 will be described in a proximal-to-distal direction along a length of the distal segment 106. Therefore, description of a component being "distal" or positioned "distally" of another portion of the distal segment 106 indicates the relative position of the portions along the length of the catheter body 102 in the distal segment 106. Unless stated otherwise, such description is not intended to limit the relative positioning of the portions with respect to the proximal segment 104 of the catheter body 102.

Figure 5:
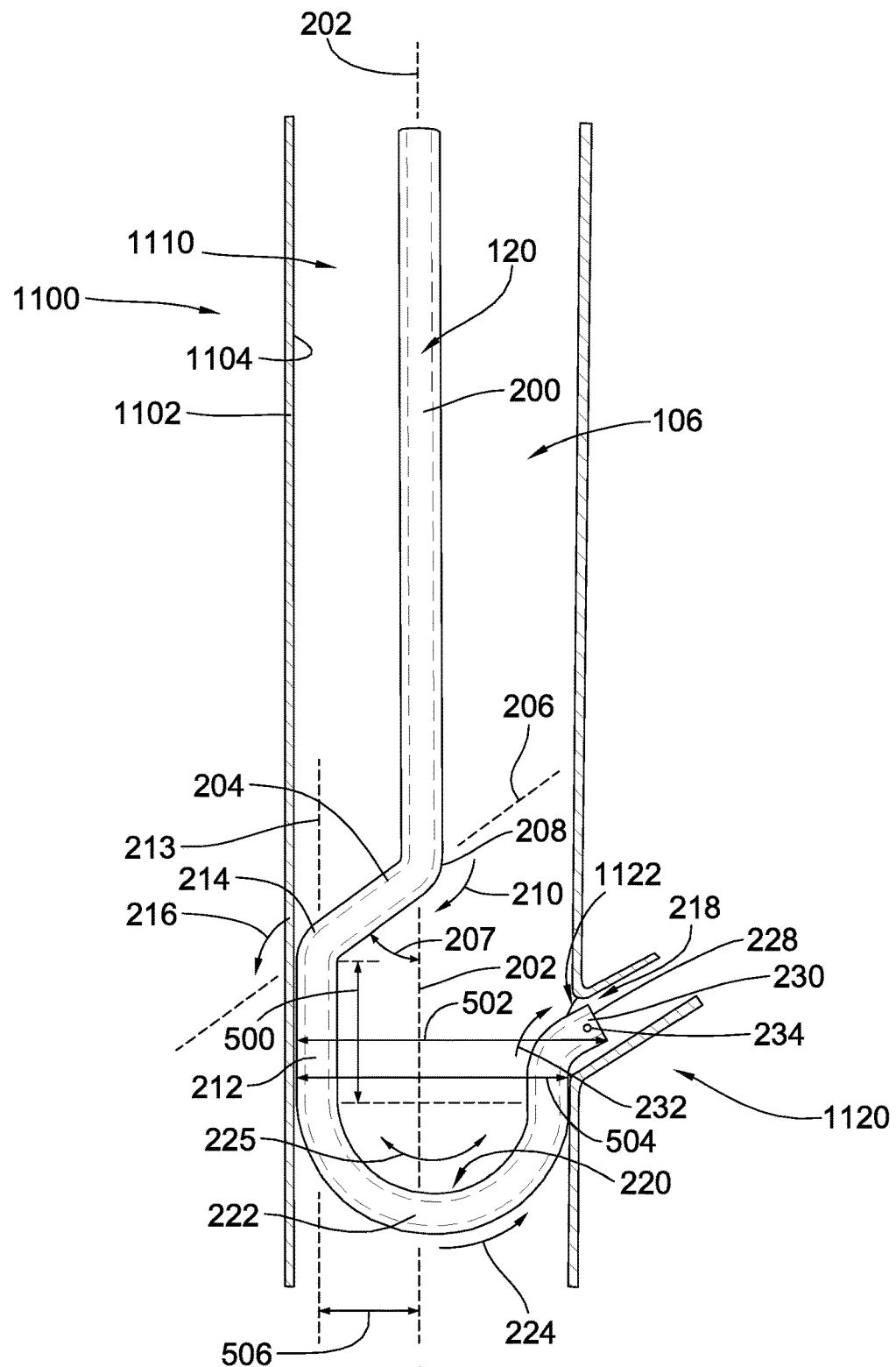
FIG. 5 illustrates a cross-sectional view of a vessel with a distal segment of a catheter body positioned within the vessel and the distal tip located within a branch vessel.

FIG. 5 illustrates a distal segment 106 of the catheter body 102 in a preformed configuration and within a vessel 1100 of a patient 1000. FIGS. 6 and 7 illustrate perspective and side views, respectively, of the distal segment 106 in the preformed configuration (aka "free state"). The distal segment 106 includes a first substantially straight portion 200 positioned distally of the proximal segment 104 of the catheter body 102. The first substantially straight portion 200 has a longitudinal axis 202 extending therethrough.

Positioned distally of the first substantially straight portion 200 is a laterally extending portion 204. Laterally extending portion 204 extends along a longitudinal axis 206 in a direction transverse to and laterally away from longitudinal axis 202 and towards the vessel wall 1102. In some instances, longitudinal axis 206 intersects longitudinal axis 202 at an angle 207 between 10° and 90°. In some instances, angle 207 is between 20° and 60°.

In some instances, positioned distally of the first substantially straight portion 200 and proximally of the laterally extending portion 204 along a length of distal segment 106 is a first curved portion 208. The first curved portion 208 can link the first substantially straight portion 200 and laterally extending portion 204 and provide a transition between the two so as to allow for a guidewire and/or microcatheter to be advanced from first substantially straight portion 200 to laterally extending portion 204. It is contemplated that the guidewire and/or microcatheter can be advanced within the catheter body 102, such as within a lumen 120 defined by the catheter body 102, and/or the microcatheter can be advanced over the catheter body 102.

First curved portion 208 curves in a first direction 210. In many instances, first direction 210 is in a direction away from a distal tip 218 of the distal segment 106. As illustrated in FIG. 5, the first direction 210 is clockwise. Additionally, the first curved portion 208 can curve through the angle of intersection between longitudinal axis 202 and longitudinal axis 206.

Positioned distally of the laterally extending portion 204 is a tip-opposing portion 212. Tip-opposing portion 212 extends along longitudinal axis 213 which lies substantially parallel to vessel wall 1102 and/or longitudinal axis 202. Tip-opposing portion 212 is diametrically opposed to the distal tip 218 of the distal segment 106 relative to longitudinal axis 202. In many instances, tip-opposing portion 212 extends for a length 500 of 30 mm or less, and in some particular arrangements, tip-opposing portion 212 extends for a length 500 of about 20 mm.

In some instances, positioned distally of laterally extending portion 204 and proximally of tip-opposing portion 212 is a second curved portion 214. Second curved portion 214 curves in a second direction 216. In many instances, a second direction 216 is opposite that of first direction 210 (i.e., second direction 216 is counter-clockwise as shown in FIG. 5) Similar to first curved portion 208 with first substantially straight portion 200 and laterally extending portion 204, second curved portion 214 can link the laterally extending portion 204 and tip-opposing portion 212 with one another so as to allow for a guidewire and/or microcatheter to be advanced from the laterally extending portion 204 to tip-opposing portion 212.

Positioned distally of the tip-opposing portion 212 is a tip-deflecting portion 220. Tip-deflecting portion 220 is arranged to deflectably support distal tip 218 relative to tip-opposing portion 212. As shown in FIG. 5, tip-deflecting portion 220 extends laterally across the vessel lumen 1110 defined by vessel wall 1102. In many instances, when projected onto a plane with longitudinal axis 202 and laterally extending portion 204, tip-deflecting portion 220 extends laterally across longitudinal axis 202 and longitudinal axis 202 can bisect tip-deflecting portion 220 into two equal portions. In some instances, tip-deflecting portion 220 extends through longitudinal axis 202.

Tip-deflecting portion 220 can include a third curved portion 222 that curves in a third direction 224 (shown as counter clockwise in FIG. 5). In several instances, when projected onto a plane with the first curved portion 208 and the second curved portion 214, the third curved portion 222 curves in the same direction as the second curved portion 214. Additionally, in some instances, third curved portion 222 and second curved portion 214 curve in a direction opposite that of the first curved portion 208. In curved configurations, tip-deflecting portion 220 curves through an angle 225 that, in many instances, is at least 160°. The third curved portion 222 can also have a radius of curvature of 18 mm or less, as measured from the outermost surface of the catheter body, for the disclosed embodiments.

Distal segment 106 terminates at distal tip 218 which, as shown in FIG. 5, is positioned distally of tip-deflecting portion 220. Distal tip 218 has a distal-most surface 228 that faces laterally outward from longitudinal axis 202. In some instances, distal-most surface 228 faces in a slight superior direction (i.e., towards the patient's head) or in a slight inferior direction (i.e., towards the patient's feet).

In some instances, positioned distally of the tip-deflecting portion 220 and proximally of distal tip 218 is a fourth curved portion 230. Fourth curved portion 230 curves away from longitudinal axis 202 and in a fourth direction 232 (shown as clockwise in FIG. 5). Fourth direction 232 is, in many instances, opposite the direction of third curved portion 222. Fourth curved portion 230 can lie in plane with tip-deflecting portion 220. Accordingly, fourth curved portion 230 can extend radially outward from longitudinal axis 202.

The catheter body 102 may have one or more side holes 234 extending through the wall of the catheter body 102 and communicating with a lumen 120 of the catheter 100. Side holes 234 may be used for the injection of contrast into the aorta and/or the branch vessel for visualization under x-ray. Side holes 234 are positioned proximal of the distal tip 218 and can be located adjacent to the distal tip or in a portion of the catheter body proximal of the distal tip. For example, side holes 234 may be positioned in the tip-deflecting portion 220, the tip-opposing portion 212, the laterally extending portion 204 and/or the first substantially straight portion 200.

When positioned within the vessel 1100 of the patient 1000, distal segment 106 extends through a length of the vessel lumen 1110 defined by vessel wall 1102. Preferably, distal segment 106 is sized and/or arranged for a target location such that when distal segment 106 is positioned at the target location, an outer surface of tip-opposing portion 212 of distal segment 106 lies against and contacts an inner surface 1104 of the vessel wall 1102 and longitudinal axis 202 is located substantially at the center of the vessel lumen 1110. In some instances, when the distal tip 218 is positioned within a branch vessel 1120, the distal segment 106 contacts a portion of inner surface 1104 of the vessel wall 1102 adjacent to the opening 1122 of the branch vessel 1120.

In the disclosed catheter arrangements, the distal segment 106 has a maximum outer dimension 502 of 35 mm or less, as measured perpendicular to the longitudinal axis from the outer-most surface of the tip-opposing portion to the outer-most portion of the distal tip. Furthermore, the tip-opposing portion 212 and tip-deflecting portion 220 of the distal segment 106 can define a shape having a maximum outer dimension 504 of 30 mm or less and/or at least 10 mm when measured perpendicular to the longitudinal axis. In some instances, outer dimension 504 is between 18 mm and 20 mm.

As mentioned above, the tip-opposing portion 212 may have a length 500 of about 20 mm, and the distal tip 218 may align laterally with the mid-point of the tip-opposing portion 212. The longitudinal axis 202 of the first substantially straight portion 200 and the longitudinal axis 213 of the tip-opposing portion 212 can be separated by a distance 506 of 15 mm or less and/or at least 5 mm. In some instances, longitudinal axis 202 and longitudinal axis 213 are separated by a distance 506 of about 10 mm.

Advantageously, the present disclosure provides catheter designs capable of securing the catheter in place and providing feedback indicative of the distal tip of the catheter being positioned in a branch vessel. For example, when the distal tip 218 of distal segment 106 is positioned within branch vessel 1120, such as that illustrated in FIG. 5, the distal segment 106 provides resistance to a withdrawing movement (e.g., moving distal segment 106 upward).

Figure 8:
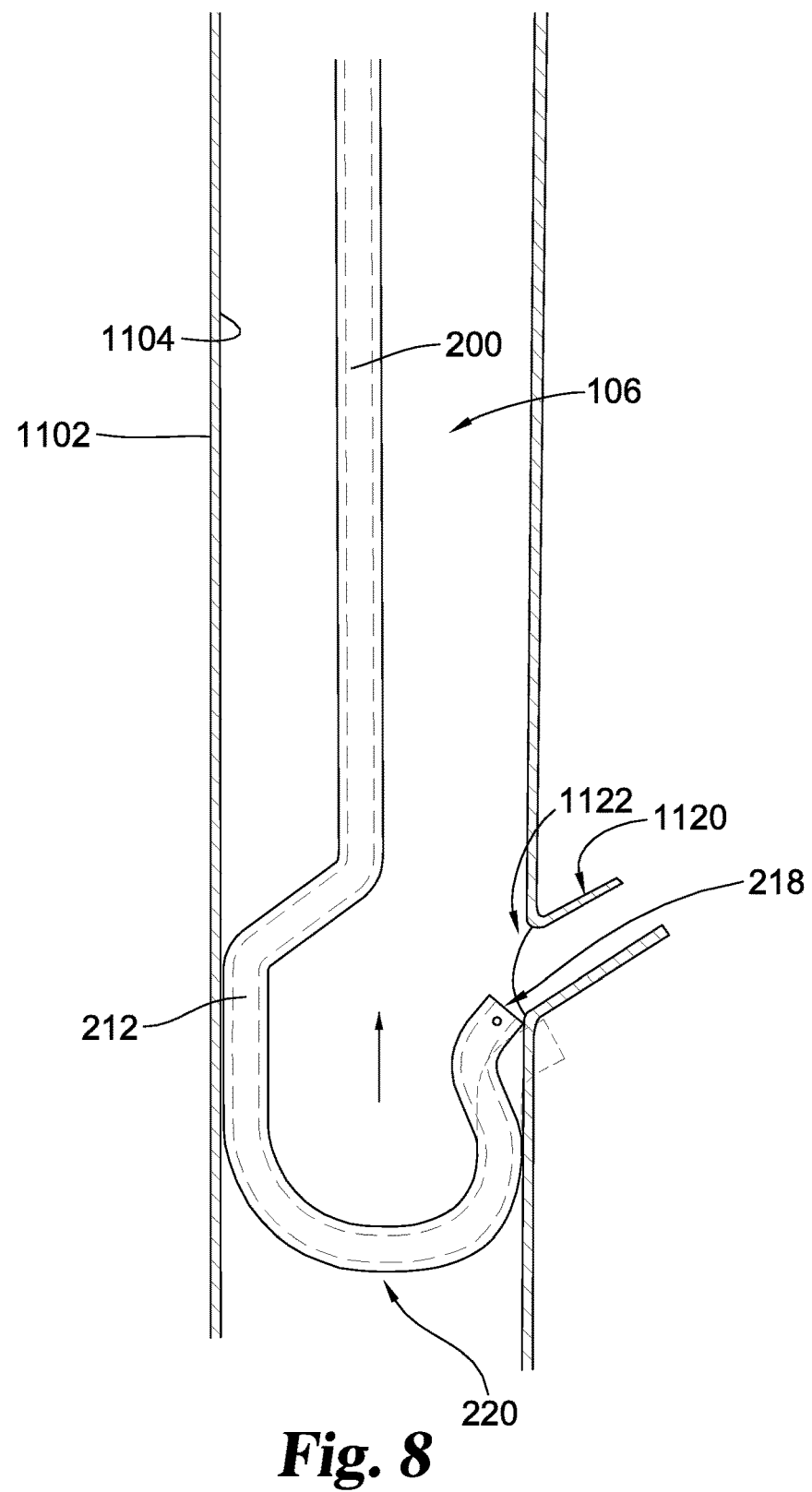
FIGS. 8, 9 and 10 illustrate cross-sectional views of a vessel with a distal segment of a catheter positioned within the vessel, with the distal tip located outside a branch vessel.
Figure 9:
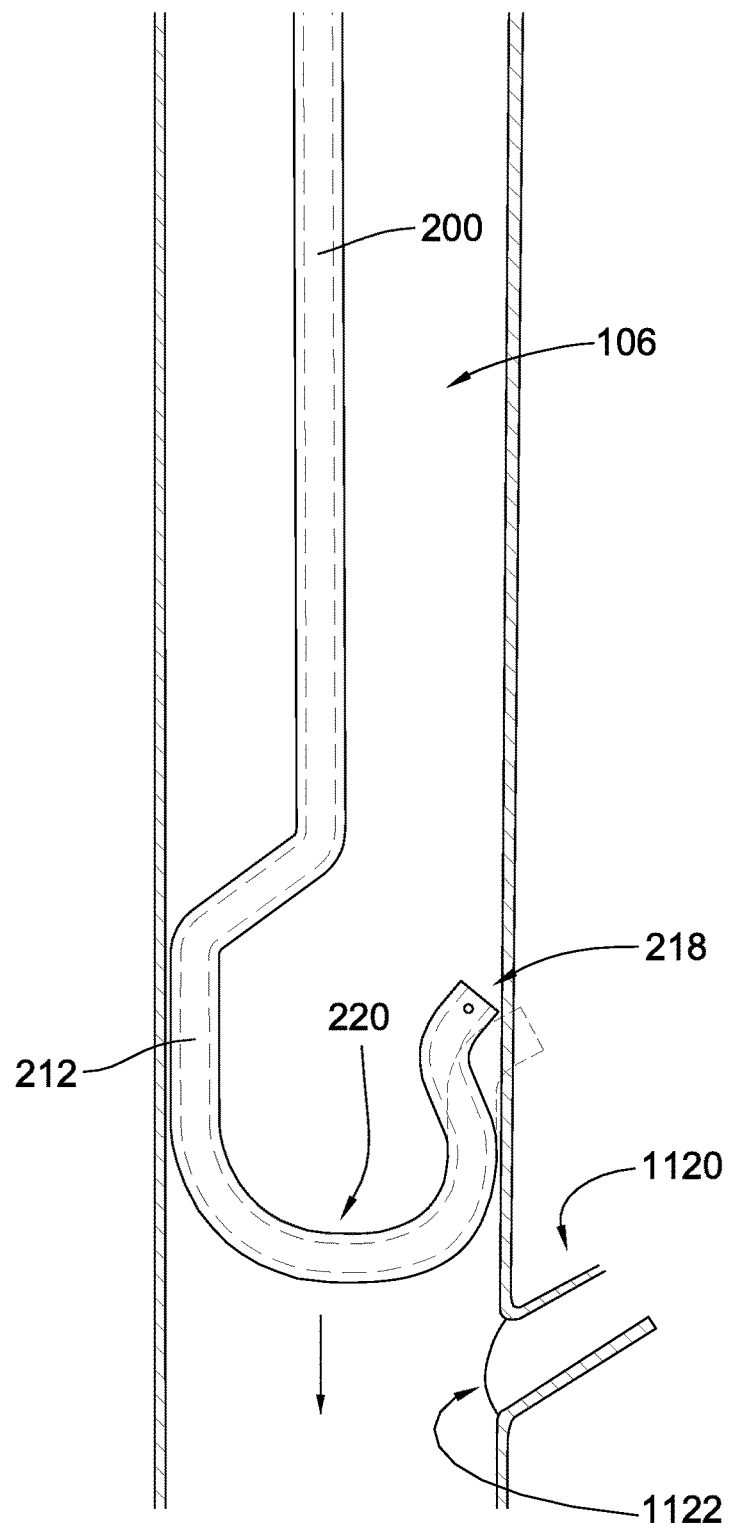

In some instances, the catheter body includes portions or markers that are visualizable under ultrasound or radiography so that an operator may visualize the shape or relative positioning of portions of distal segment 106. Advantageously, such an arrangement can allow a medical professional to observe distal segment 106 change from a deflected or compressed configuration into the preformed configuration, which can be indicative of distal tip 218 being positioned within an opening in the vessel wall 1102, such as an opening to a branch vessel or an aneurysm. FIGS. 8 and 9 illustrate such an arrangement. In FIGS. 8 and 9, distal segment 106 of catheter body 102 is in a compressed configuration in which the tip-deflecting portion 220 and distal tip 218 are in contact with the inner surface 1104 of the vessel wall 1102 and are deflected inwardly (e.g., towards tip-opposing portion 212) by the force from the vessel wall 1102. The preformed "free" or "unstressed" configuration of the tip-deflecting portion 220 and distal tip 218 are illustrated by the phantom lines in FIGS. 8 and 9. Under ultrasonic and/or radiographic imaging, a medical professional could observe the inward deflection of distal tip 218 relative to the configuration illustrated in FIG. 5 and therefore know that distal tip 218 is not positioned within a branch vessel.

Figure 10:
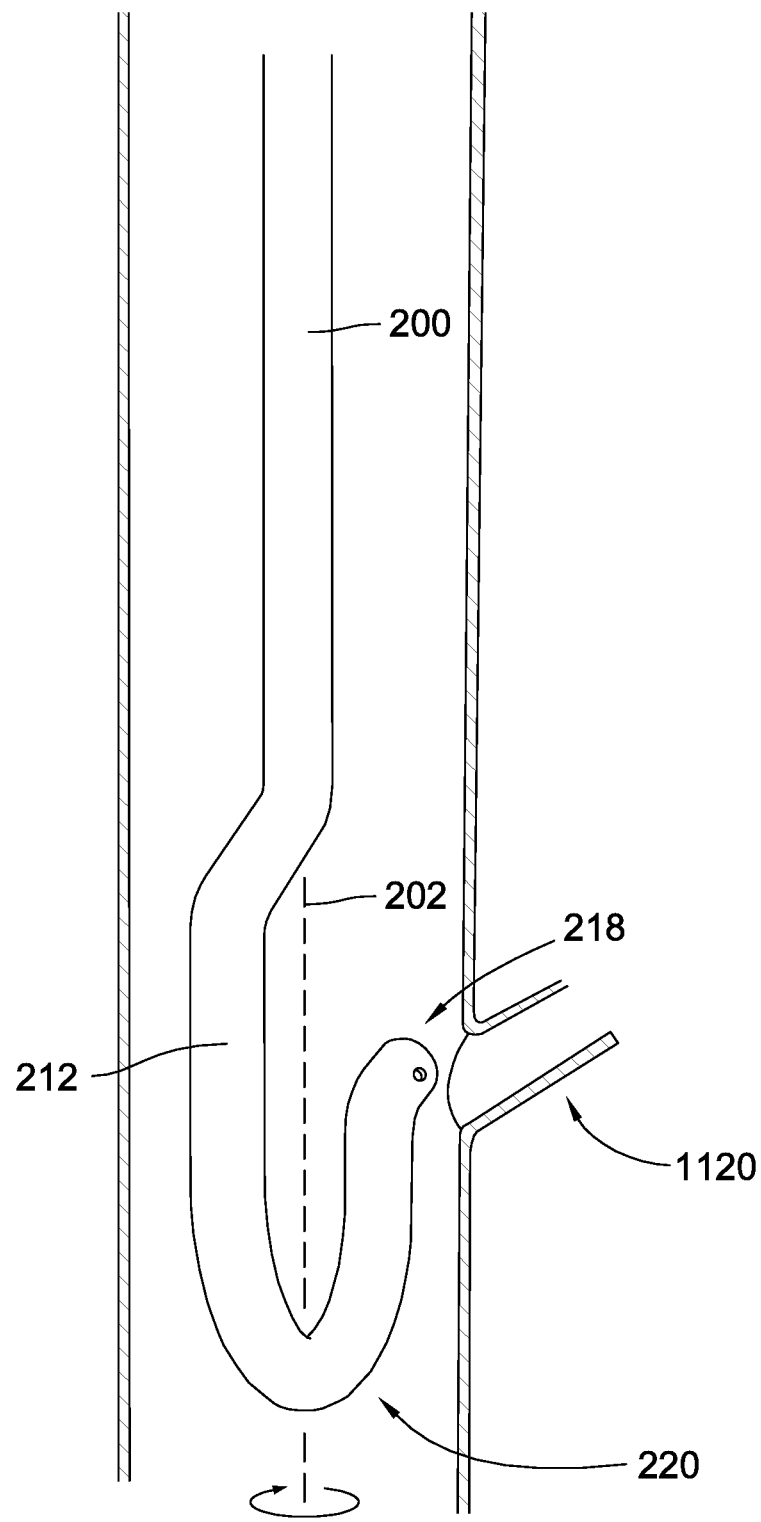
Figure 11:
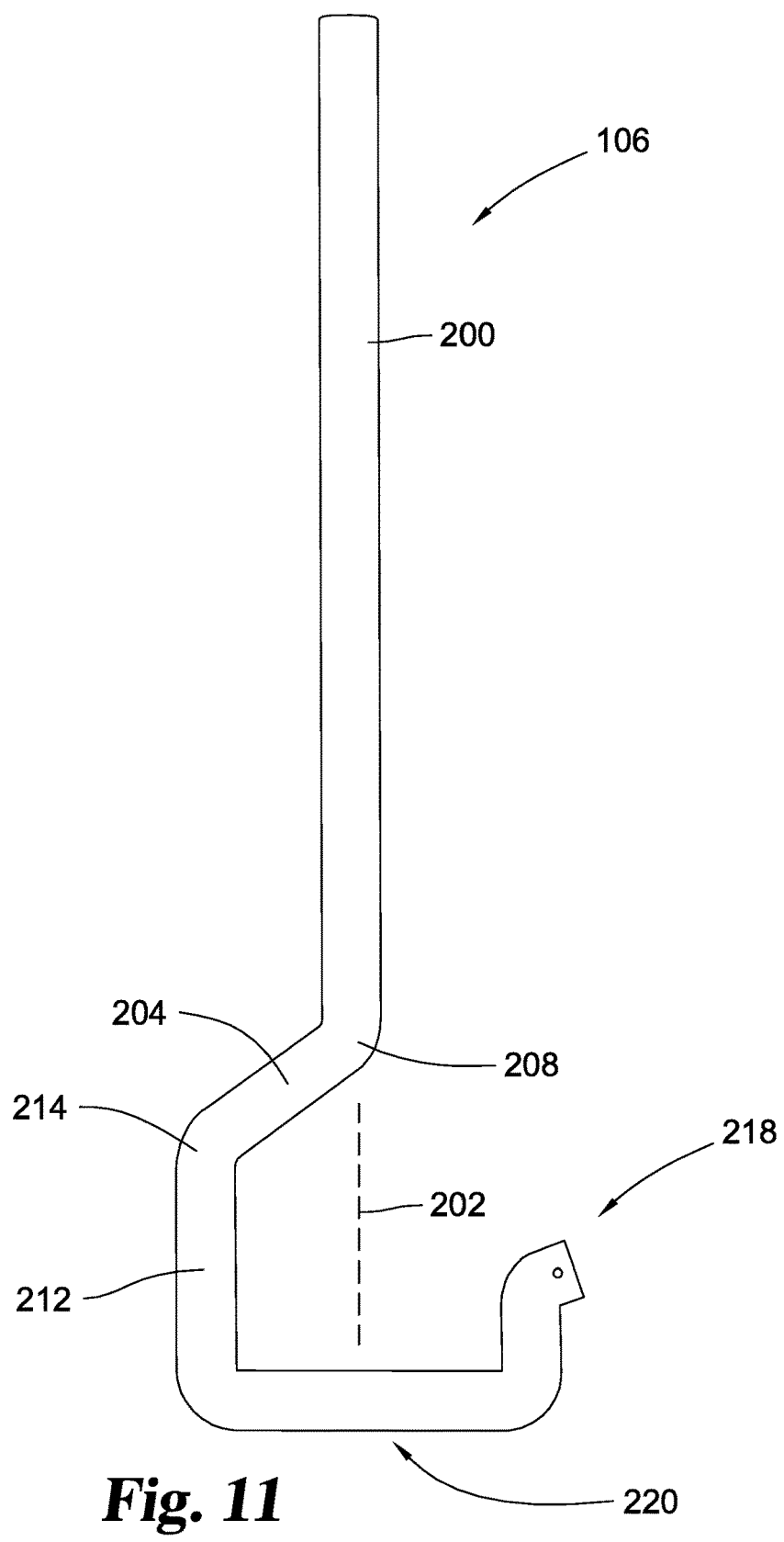
FIG. 11 illustrates a front view of a variation of a distal segment of a catheter body.
Figure 12:
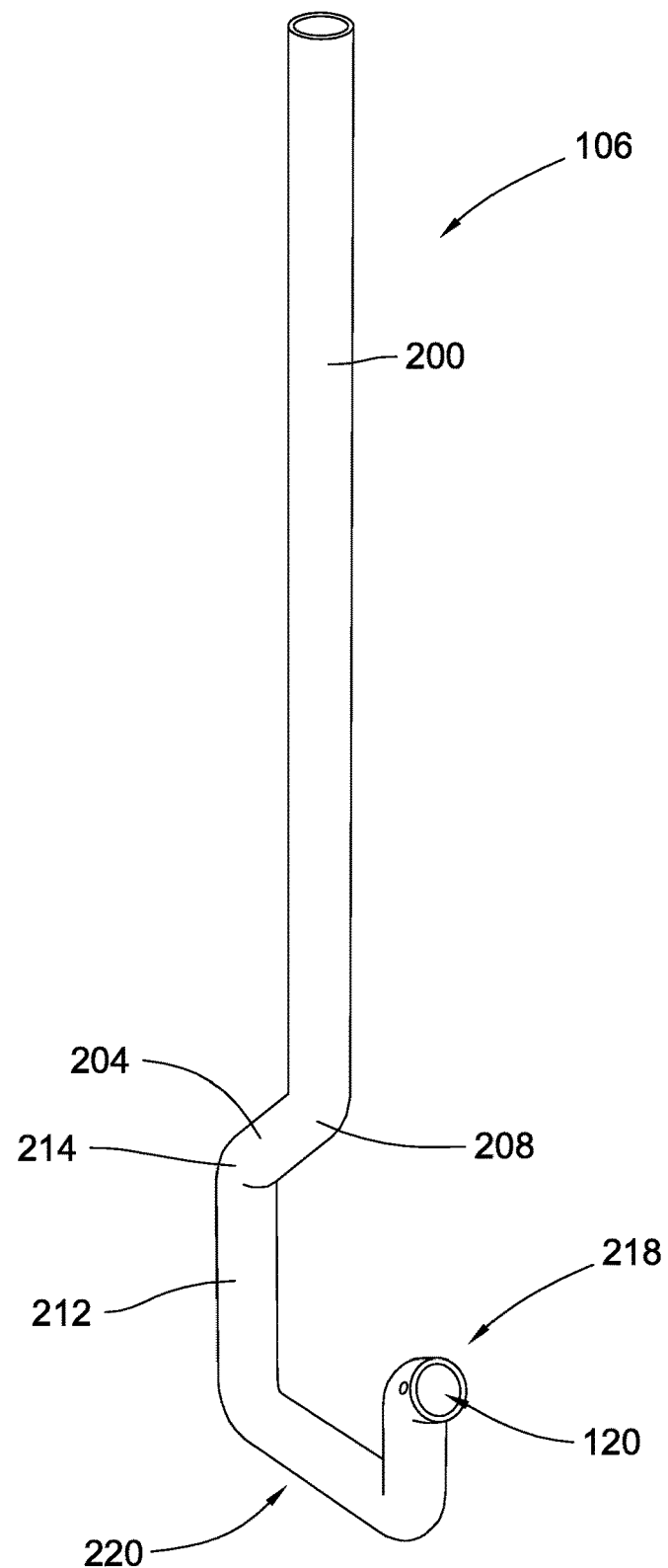
FIG. 12 illustrates a perspective view of the distal segment illustrated in FIG. 11.

Advantageously, the catheter designs the present disclosure also aid in the positioning and/or repositioning of distal segment 106 within the body the patient so that distal tip 218 may be located within a branch vessel. From the position illustrated in FIG. 8, distal segment 106 can be withdrawn in a proximal direction (i.e., towards proximal segment 104 and illustrated by the arrow in FIG. 8) to align distal tip 218 with opening 1122 to branch vessel 1120. Similarly, in FIG. 9 distal segment 106 may be advanced in a distal direction (illustrated by the arrow in FIG. 9) to align distal tip 218 with opening 1122 of branch vessel 1120. Furthermore, as illustrated in FIG. 10, distal segment 106 can be rotated around longitudinal axis 202, such as in the direction indicated in the arrow in FIG. 10, to align distal tip 218 with an opening 1122 to a branch vessel 1120.

The catheter designs disclosed herein advantageously position the tip-opposing portion 212 and distal tip 218 in diametric opposition within the vessel lumen 1110. This diametric opposition orients distal tip 218 to extend radially outward from the center of the vessel lumen 1110 (located along longitudinal axis 202) and therefore position distal tip 218 to enter a vessel opening 1122 along a substantially orthogonal direction. Accessing the openings to smaller vessels can be difficult if approached from a non-orthogonal angle. Advantageously, approaching the vessel opening along a substantially orthogonal direction provides a larger "opening" through which to enter the vessel. The designs are therefore capable of accessing relatively small vessel openings.

Additionally, catheter designs disclosed herein are torquable and arranged to rotate the distal tip of the catheter body around an axis that is spaced from the vessel wall. In some instances, the axis of rotation is located at the center of the vessel lumen 1110. For example, laterally extending portion 204, tip-opposing portion 212, tip-deflecting portion 220 and distal tip 218 can orient first substantially straight portion 200 and longitudinal axis 202 along the central axis of the vessel lumen 1110. Additionally, as described above, first substantially straight portion 200 has a longitudinal axis 202 that extends between tip-opposing portion 212 and distal tip 218 and can, in some instances, bisect tip-deflecting portion 220. When first substantially straight portion 200 is positioned centrally within lumen 1110 of vessel 1100, rotation of first substantially straight portion 200 around longitudinal axis 202 will also rotate tip-opposing portion 212 and distal tip 218 around longitudinal axis 202 and, in some instances, the center of the vessel lumen 1110. Rotating distal tip 218 around an axis spaced from a wall of the vessel can position distal tip 218 substantially orthogonal to the vessel opening 1122 and can thereby aid in positioning the distal tip in the branch vessel.

FIGS. 11-14 illustrate variations of distal segment 106 of catheter body 102. The variations illustrated in FIGS. 11-14 can be used in the same methods and positioned in the same manners described above. Therefore, much of the above disclosure will not be repeated. In contrast to the other illustrated embodiments, the distal segment 106 shown in FIGS. 11 and 12 has a substantially-straight tip-deflecting portion 220 extending between tip-opposing portion 212 and distal tip 218. Advantageously, this arrangement can be used to access openings located close to the bifurcation of the abdominal aorta as the "flat" bottom of the distal segment 106 can allow the distal tip 218 to be advanced further in an inferior direction than other arrangements.

Figure 13:
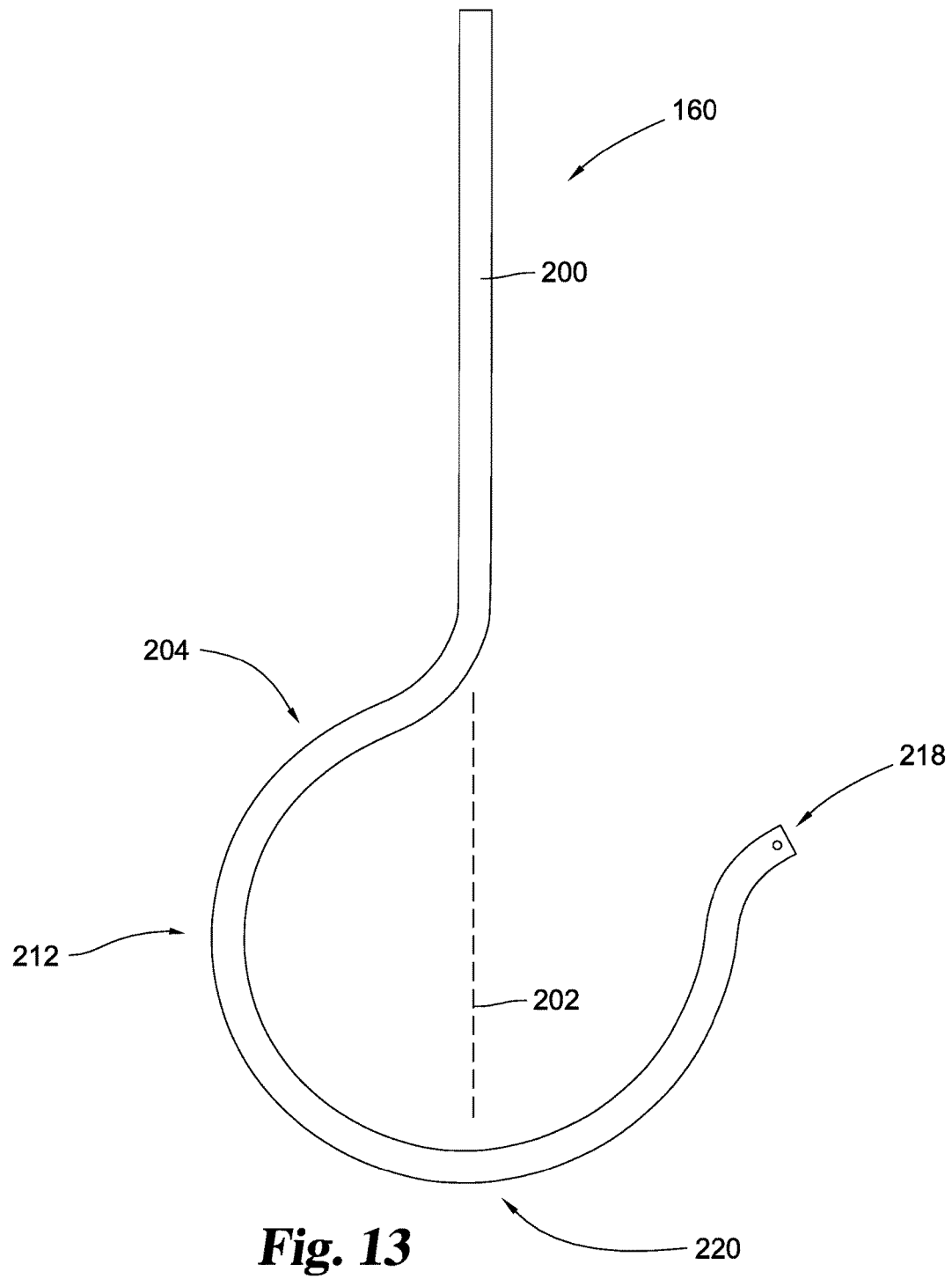
FIG. 13 illustrates a front view of a variation of a distal segment of a catheter body.
Figure 14:
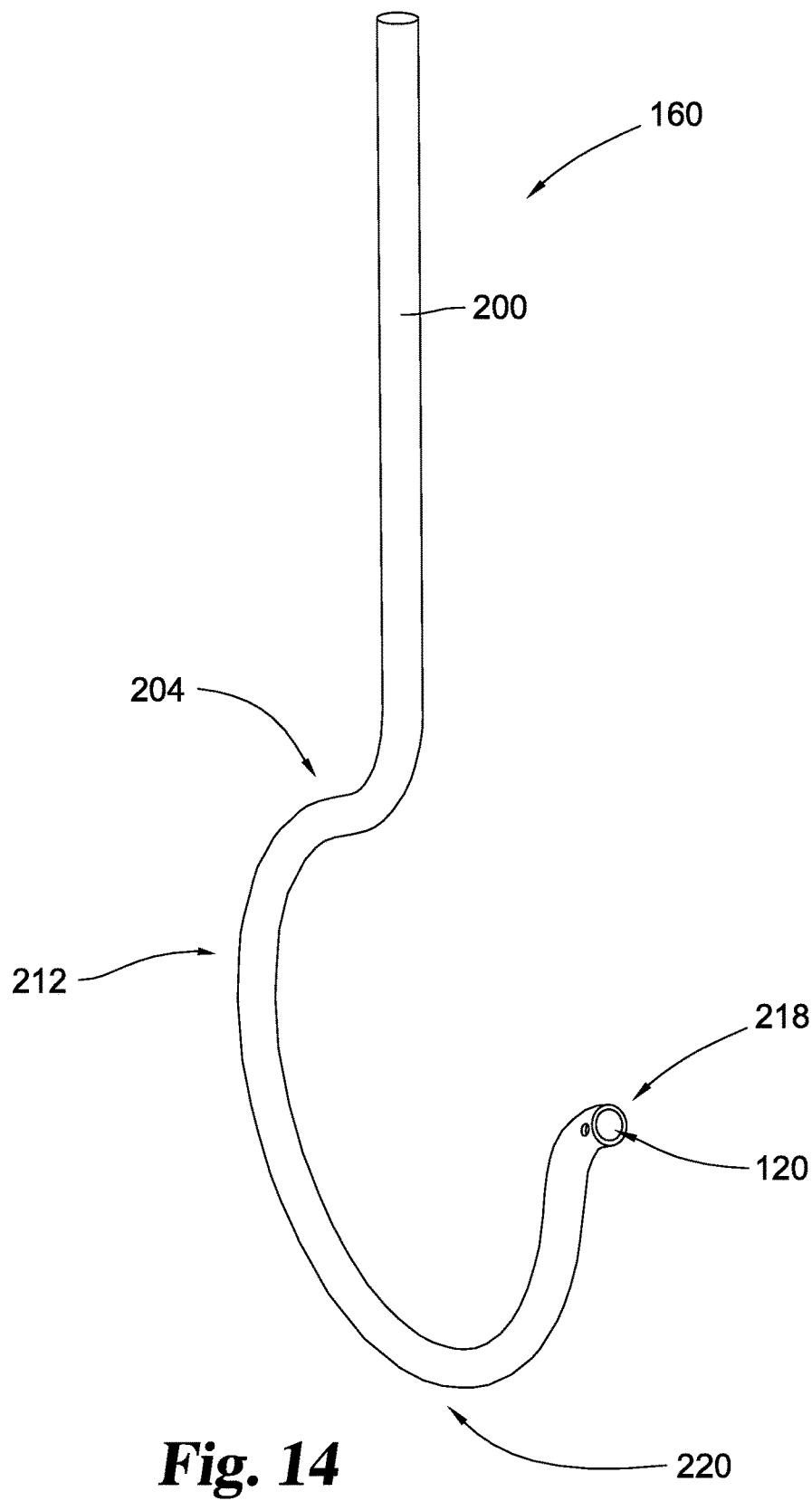
FIG. 14 illustrates a perspective view of the distal segment illustrated in FIG. 13.

FIGS. 13 and 14 illustrate yet another variation in which the length of the distal segment 106 extending distally from the first substantially straight portion 200 comprises a series of contiguous curves. For example, laterally extending portion 204, tip-opposing portion 212, and tip-deflecting portion 220 may comprise a series of continuous curves extending from the first substantially straight portion 200 to distal tip 218. Advantageously, this arrangement provides smooth transitions between the portions of the distal segment 106 and therefore can ease passage of a guidewire and/or micro-catheter through lumen 120 of the catheter body 102 and/or advancement of a sheath over the outer surface of catheter body 102.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The following numbered clauses set out specific embodiments that may be useful in understanding the present invention:

1. A method of accessing a branch vessel of the abdominal aorta of a patient, comprising:

advancing a catheter body in an insertable configuration into an artery of an arm of the patient and through the body of the patient towards and into the abdominal aorta, the catheter body and configurable from the insertable configuration to a preformed configuration;

configuring a distal segment of the catheter body into the preformed configuration, wherein the distal segment in the preformed configuration has a length that includes a first substantially straight portion, a laterally extending portion, a tip-opposing portion, a tip-deflecting portion, and a distal tip, wherein the first substantially straight portion has a longitudinal axis, wherein the laterally extending portion is positioned distally of the first substantially straight portion along the length of the distal segment and extends laterally away from the longitudinal axis, wherein the tip-opposing portion is positioned distally of the laterally extending portion along the length of the distal segment and extends substantially parallel to and offset from the longitudinal axis, wherein the tip-deflecting portion is positioned distally of the tip-opposing portion along the length of distal segment and extends laterally past the longitudinal axis, wherein the distal tip is positioned distally of the tip-deflecting portion along the length of the distal segment and is diametrically opposed to the tip-opposing portion relative to the longitudinal axis, wherein the tip-deflecting portion deflectably supports the distal tip relative to the tip-opposing portion so that the distal tip is deflectable towards the tip-opposing portion upon an external force; and positioning the distal tip within the branch vessel of the abdominal aorta.

2. The method of clause 1, wherein:

advancing the catheter body in an insertable configuration includes advancing the catheter body in an insertable configuration over a guidewire.

3. The method of any one of the preceding clauses, wherein:

configuring a distal segment of the catheter body into the preformed configuration includes withdrawing the guidewire from within the catheter body so as to configure the distal segment of the catheter body into the preformed configuration.

4. The method of any one of the preceding clauses, wherein:

positioning the distal tip within a branch vessel includes rotating a proximal segment of the catheter body so as to rotate the tip-opposing portion and distal tip around the longitudinal axis.

5. A catheter useful for accessing a branch vessel of the abdominal aorta of a patient, comprising:
a catheter body having a proximal segment and a distal segment;
the distal segment having a preformed configuration and a length that includes a first substantially straight portion, a laterally extending portion, a tip-opposing portion, a tip-deflecting portion and a distal tip;
the first substantially straight portion having a longitudinal axis;
the laterally extending portion positioned distally of the first substantially straight portion along the length of the distal segment and extending laterally away from the longitudinal axis;
the tip-opposing portion positioned distally of the laterally extending portion along the length of the distal segment and extending substantially parallel to and offset from the longitudinal axis;
the tip-deflecting portion positioned distally of the tip-opposing portion along the length of distal segment and extending laterally across the longitudinal axis when projected onto a plane with the longitudinal axis and the laterally extending portion; and
the distal tip positioned distally of the tip-deflecting portion along the length of the distal segment and laterally opposite the tip-opposing portion relative to the longitudinal axis;
wherein the distal tip is deflectably supported by the tip-deflecting portion and is deflectable towards the tip-opposing portion.

6. The catheter of clause 5, wherein:
the tip-opposing portion is arranged to rest against an inner surface of the abdominal aorta of a patient and the tip-deflecting portion is arranged to extend radially across the abdominal aorta and position the distal tip in an opening of a branch vessel extending from the abdominal aorta.

7. The catheter of clause 5 or 6, wherein:
the distal tip is diametrically opposed to said tip-opposing portion relative to the longitudinal axis.

8. The catheter of any one of clauses 5-7, wherein:
the tip-deflecting portion defines a curve with a center of curvature positioned on the longitudinal axis.

9. The catheter of any one of clauses 5-8, wherein:
the tip-deflecting portion defines a curve that curves through at least 160°.

10. The catheter of any one of clauses 5-9, wherein:
the tip-deflecting portion extends through the longitudinal axis.

11. The catheter of any one of clauses 5-10, wherein:
the longitudinal axis bisects the tip-deflecting portion.

12. The catheter of any one of clauses 5-11, wherein:
the tip-opposing portion and tip-deflecting portion of the distal segment define a shape having a maximum outer dimension of 30 mm or less when measured perpendicular to the longitudinal axis of the first substantially straight portion.

13. The catheter of any one of clauses 5-12, wherein:
the tip-opposing portion and tip-deflecting portion define a shape having a maximum outer dimension of at least 10 mm when measured perpendicular to the longitudinal axis.

14. The catheter of any one of clauses 5-13, wherein:
the tip-opposing portion and tip-deflecting portion define a shape having a maximum outer dimension of 18 mm to 20 mm when measured perpendicular to the longitudinal axis.

15. The catheter of any one of clauses 5-14, wherein:
the tip-opposing portion has a longitudinal axis and the distance between the longitudinal axis of the first substantially straight portion and the longitudinal axis of the tip-opposing portion is 15 mm or less.

16. A catheter, comprising:
a catheter body having proximal segment and a distal segment, the proximal segment substantially straight under a free state and a distal segment having a curved shape under a free state,
the distal segment including:
a first substantially straight portion, a first curved portion, a laterally extending portion, a second curved portion, a tip-opposing portion, a tip-deflecting portion, and a distal tip positioned in that order in a proximal to distal direction along a length of the distal segment;
the first substantially straight portion having a longitudinal axis; the first curved portion connecting the first substantially straight portion and the laterally extending portion;
the laterally extending portion extending transverse to and laterally away from the longitudinal axis;
the second curved portion connecting the laterally extending portion and the tip-opposing portion;
the tip-opposing portion extending substantially parallel to and offset from the longitudinal axis; and
the tip-deflecting portion connecting the tip-opposing portion and the distal tip;
wherein the distal tip is deflectable supported by the tip-deflecting portion so that the distal tip may deflect towards the tip-opposing portion when subjected to an external force; and
wherein the distal segment defines a shape having a maximum outer dimension of 30 mm or less when measured perpendicular to the longitudinal axis.

17. The catheter of clause 16, wherein:
the distal tip is diametrically opposed to said tip-opposing portion relative to the longitudinal axis.

18. The catheter of clause 16 or 17, wherein:
the longitudinal axis extends through the tip-deflecting portion.

19. The catheter of any one of clauses 5-18, wherein:
tip-opposing portion has a length of at least 10 mm.

20. The catheter of any one of clauses 16-19, wherein:
the tip-opposing portion has a longitudinal axis and the distance between the longitudinal axis of the first substantially straight portion and the longitudinal axis of the tip-opposing portion is 15 mm or less.

21. A catheter, comprising:
a catheter body having proximal segment and a distal segment, the proximal segment substantially straight under a free state and a distal segment having a curved shape under a free state,
the distal segment including:
a first substantially straight portion, a first curved portion, a laterally extending portion, a second curved portion, a tip-opposing portion, a third curved portion, and a distal tip positioned in that order in a proximal to distal direction along a length of the distal segment;
the first substantially straight portion having a longitudinal axis;
the first curved portion connecting the first substantially straight portion and the laterally extending portion;
the laterally extending portion extending transverse to and laterally away from the longitudinal axis;
the second curved portion connecting the laterally extending portion and the tip-opposing portion;
the tip-opposing portion extending substantially parallel to and offset from the longitudinal axis; and the third curved portion connecting the tip-opposing portion and the distal tip;
    wherein the longitudinal axis bisects the third curved portion.
22. The catheter of any one of clauses 5-21, wherein:
    the distal segment has a maximum outer dimension of 35 mm or less, as measured perpendicular to the longitudinal axis from the outer-most surface of the tip-opposing portion to the outermost portion of the distal tip.
23. The catheter of any one of clauses 5-22, wherein:
    the tip-opposing portion has a longitudinal axis and the distance between the longitudinal axis of the first substantially straight portion and the longitudinal axis of the tip-opposing portion is about 10 mm.

The invention claimed is:

1. A method of accessing a branch vessel of an abdominal aorta of a body of a patient, comprising:
    advancing a catheter body in an insertable configuration into an artery of an arm of the patient and through the body of the patient over a guidewire towards and into the abdominal aorta, the catheter body being configurable from the insertable configuration to a preformed configuration;
    configuring a distal segment of the catheter body into the preformed configuration in the abdominal aorta by withdrawing said guidewire relative to said catheter body, wherein the distal segment of the catheter body in the preformed configuration has a length that includes a first substantially straight portion, a laterally extending portion, a tip-opposing portion, a tip-deflecting portion, and a distal tip, wherein the first substantially straight portion has a longitudinal axis, wherein the laterally extending portion is positioned distally of the first substantially straight portion along the length of the distal segment of the catheter body and extends laterally away from the longitudinal axis, wherein the tip-opposing portion is positioned distally of the laterally extending portion along the length of the distal segment of the catheter body and extends substantially parallel to and offset from the longitudinal axis, wherein the tip-deflecting portion is positioned distally of the tip-opposing portion along the length of distal segment and extends laterally past the longitudinal axis, wherein the distal tip is positioned distally of the tip-deflecting portion along the length of the distal segment of the catheter body and is diametrically opposed to the tip-opposing portion relative to the longitudinal axis, wherein the tip-deflecting portion deflectably supports the distal tip relative to the tip-opposing portion so that the distal tip is deflectable towards the tip-opposing portion upon an external force; and then
    positioning the distal tip within the branch vessel of the abdominal aorta.

2. The method of claim 1, wherein:
    positioning the distal tip within the branch vessel includes rotating a proximal segment of the catheter body so as to rotate the tip-opposing portion and the distal tip around the longitudinal axis.

3. The method of claim 1, wherein:
    the catheter body in an insertable configuration having a length of at least 110 cm is advanced through a radial artery.

4. A catheter useful for accessing a branch vessel of the abdominal aorta of a patient, comprising:
    a catheter body having a proximal segment and a distal segment having a length of at least 110 cm;
    the distal segment having a preformed configuration and a length that includes a first substantially straight portion, a laterally extending portion, a tip-opposing portion, a tip-deflecting portion and a distal tip;
    the first substantially straight portion having a longitudinal axis;
    the laterally extending portion positioned distally of the first substantially straight portion along the length of the distal segment and extending laterally away from the longitudinal axis;
    the tip-opposing portion positioned distally of the laterally extending portion along the length of the distal segment and extending substantially parallel to and offset from the longitudinal axis;
    the tip-deflecting portion positioned distally of the tip-opposing portion along the length of distal segment and extending laterally across the longitudinal axis when projected onto a plane with the longitudinal axis and the laterally extending portion; and
    the distal tip positioned distally of the tip-deflecting portion along the length of the distal segment and laterally opposite the tip-opposing portion relative to the longitudinal axis;
    wherein the distal tip is deflectably supported by the tip-deflecting portion and is deflectable towards the tip-opposing portion.

5. The catheter of claim 4, wherein:
    the tip-opposing portion is arranged to rest against an inner surface of the abdominal aorta of a patient and the tip-deflecting portion is arranged to extend radially across the abdominal aorta and position the distal tip in an opening of a branch vessel extending from the abdominal aorta.

6. The catheter of claim 4, wherein:
    the distal tip is diametrically opposed to said tip-opposing portion relative to the longitudinal axis.

7. The catheter of claim 4, wherein:
    the tip-deflecting portion defines a curve with a center of curvature positioned on the longitudinal axis.

8. The catheter of claim 4, wherein:
    the tip-deflecting portion defines a curve that curves through at least 160°.

9. The catheter of claim 4, wherein:
    the tip-deflecting portion extends through the longitudinal axis.

10. The catheter of claim 4, wherein:
    the longitudinal axis bisects the tip-deflecting portion.

11. The catheter of claim 4, wherein:
    the tip-opposing portion and tip-deflecting portion of the distal segment define a shape having a maximum outer dimension of 30 mm or less when measured perpendicular to the longitudinal axis of the first substantially straight portion.

12. The catheter of claim 11, wherein:
    the tip-opposing portion and tip-deflecting portion define a shape having a maximum outer dimension of at least 10 mm when measured perpendicular to the longitudinal axis.

13. The catheter of claim 12, wherein:
    the tip-opposing portion and tip-deflecting portion define a shape having a maximum outer dimension of 18 mm to 20 mm when measured perpendicular to the longitudinal axis.

14. The catheter of claim 4, wherein:
    the tip-opposing portion has a longitudinal axis and the distance between the longitudinal axis of the first substantially straight portion and the longitudinal axis of the tip-opposing portion is 15 mm or less.

15. A catheter, comprising:
a catheter body having proximal segment and a distal segment having a length of at least 110 cm, the proximal segment substantially straight under a free state and a distal segment having a curved shape under a free state,
the distal segment including:
- a first substantially straight portion, a first curved portion, a laterally extending portion, a second curved portion, a tip-opposing portion, a tip-deflecting portion, and a distal tip positioned in that order in a proximal to distal direction along a length of the distal segment;
- the first substantially straight portion having a longitudinal axis;
- the first curved portion connecting the first substantially straight portion and the laterally extending portion;
- the laterally extending portion extending transverse to and laterally away from the longitudinal axis;
- the second curved portion connecting the laterally extending portion and the tip-opposing portion;
- the tip-opposing portion extending substantially parallel to and offset from the longitudinal axis; and
- the tip-deflecting portion connecting the tip-opposing portion and the distal tip;
- wherein the distal tip is deflectably supported by the tip-deflecting portion so that the distal tip may deflect towards the tip-opposing portion when subjected to an external force; and
- wherein the tip-opposing portion is arranged to rest against an inner surface of the abdominal aorta of a patient and the tip-deflecting portion is arranged to extend radially across the abdominal aorta and position the distal tip in an opening of a branch vessel extending from the abdominal aorta.

16. The catheter of claim 15, wherein:
the longitudinal axis extends through the tip-deflecting portion.

17. The catheter of claim 15, wherein:
tip-opposing portion has a length of at least 10 mm.

18. The catheter of claim 15, wherein:
the tip-opposing portion has a longitudinal axis and the distance between the longitudinal axis of the first substantially straight portion and the longitudinal axis of the tip-opposing portion is 15 mm or less.

19. A catheter, comprising:
a catheter body having proximal segment and a distal segment, the proximal segment substantially straight under a free state and a distal segment having a curved shape under a free state,
the distal segment including:
- a first substantially straight portion, a first curved portion, a laterally extending portion, a second curved portion a tip-opposing portion, a tip-deflecting portion, and a distal tip positioned in that order in a proximal to distal direction along a length of the distal segment;
- the first substantially straight portion having a longitudinal axis;
- the first curved portion connecting the first substantially straight portion and the laterally extending portion;
- the laterally extending portion extending transverse to and laterally away from the longitudinal axis;
- the second curved portion connecting the laterally extending portion and the tip-opposing portion;
- the tip-opposing portion extending substantially parallel to and offset from the longitudinal axis; and
- the tip-deflecting portion connecting the tip-opposing portion and the distal tip;
- wherein the distal tip is deflectably supported by the tip-deflecting portion so that the distal tip may deflect towards the tip-opposing portion when subjected to an external force;
- wherein the tip-opposing portion is arranged to rest against an inner surface of the abdominal aorta of a patient and the tip-deflecting portion is arranged to extend radially across the abdominal aorta and position the distal tip in an opening of a branch vessel extending from the abdominal aorta; and
wherein
the distal tip is diametrically opposed to said tip-opposing portion relative to the longitudinal axis.

* * * * *

UNITED STATES PATENT AND TRADEMARK OFFICE
CERTIFICATE OF CORRECTION

PATENT NO.         : 10,434,287 B2                                Page 1 of 1
APPLICATION NO.    : 15/096977
DATED              : October 8, 2019
INVENTOR(S)        : Clint Merkel It is certified that error appears in the above-identified patent and that said Letters Patent is hereby corrected as shown below:

On the Title Page

In the Title:
Please Change "CATHERER" to --CATHETER--

Signed and Sealed this
Third Day of December, 2019

Andrei Iancu
*Director of the United States Patent and Trademark Office*